United States Patent [19]
Schmelzer et al.

[11] Patent Number: 5,196,594
[45] Date of Patent: Mar. 23, 1993

[54] PROCESS FOR THE PRODUCTION OF 4,4'-DIAMINO-DICYCLOHEXYLMETHANE WITH A LOW TRANS-TRANS ISOMER CONTENT BY THE CATALYTIC HYDROGENATION OF 4,4'-DIAMINO-DIPHENYLMETHANE

[75] Inventors: George H. Schmelzer, Pittsburgh, Pa.; Gary F. Allen, New Martinsville, W. Va.; Guenther K. H. Bub, Marl; Werner Otte, Dorsten, both of Fed. Rep. of Germany

[73] Assignees: Miles, Inc., Pittsburgh, Pa.; Huls Aktiengesellschaft, Marl, Fed. Rep. of Germany

[21] Appl. No.: 410,382

[22] Filed: Sep. 21, 1989

Related U.S. Application Data

[63] Continuation of Ser. No. 143,884, Jan. 14, 1988, abandoned.

[51] Int. Cl.$^5$ ............................................. C07C 211/35
[52] U.S. Cl. .................................................... 564/452
[58] Field of Search ........................................ 564/452

[56] References Cited

U.S. PATENT DOCUMENTS

| | | | |
|---|---|---|---|
| 2,511,028 | 6/1950 | Whitman | 564/452 |
| 2,606,924 | 8/1952 | Whitman | 564/452 |
| 3,743,677 | 7/1973 | Grossjubsjt et al. | 260/563 D |
| 3,766,272 | 11/1973 | Brake et al. | 260/563 B |
| 4,394,523 | 7/1983 | Allen | 564/451 |

FOREIGN PATENT DOCUMENTS 1122609 8/1968 United Kingdom .

Primary Examiner—C. Warren Ivy
Assistant Examiner—Ba K. Trinh
Attorney, Agent, or Firm—Joseph C. Gil; Thomas W. Roy

[57] ABSTRACT

The present invention is directed to a process for the catalytic hydrogenation of a starting material containing 4,4'-diamino-diphenylmethane (4,4'-MDA) or its mixtures with 2,4'-diamino-diphenylmethane, 2,2'-diamino-diphenylmethane and/or higher ring compounds of the diphenylmethane series to a hydrogenation product having a trans-trans isomer content of 4,4'-diamino-dicyclohexylmethane (4,4'-HMDA) of about 15 to 40 weight percent, based on the diamine content of the hydrogenated product, by continuously hydrogenating in at least one fixed bed reactor at a temperature of about 100° to 190° C. and a pressure of about 50 to 350 bar in the presence of a ruthenium catalyst on a catalyst support having a BET surface area of about 70 to 280 m$^2$/g and an average pore diameter $d_p$ of about 10 to 320 Å, the catalyst being prepared by impregnating the catalyst support to a penetration depth of at least about 50 μm with a soluble ruthenium compound in an amount sufficient to provide a catalyst containing about 0.1 to 5 weight percent ruthenium and subsequently reducing the soluble ruthenium compound to ruthenium.

13 Claims, No Drawings

__PROCESS FOR THE PRODUCTION OF 4,4'-DIAMINO-DICYCLOHEXYLMETHANE WITH A LOW TRANS-TRANS ISOMER CONTENT BY THE CATALYTIC HYDROGENATION OF 4,4'-DIAMINO-DIPHENYLMETHANE__

This application is a continuation, of application Ser. No. 07/143,884 filed Jan. 14, 1988, now abandoned.

BACKGROUND OF THE INVENTION

1. Field of the Invention

The present invention is directed to a process for the production of 4,4'-diamino-dicyclohexylmethane with a low trans-trans isomer content by the catalytic hydrogenation of 4,4'-diamino-diphenylmethane.

2. Description of the Prior Art

In order to obtain a diisocyanate, which is liquid at room temperature, through the phosgenation of 4,4'-diamino-dicyclohexylmethane (4,4'-HMDA) or its mixtures with the 2,4'-and/or 2,2'-HMDA isomers, the content of the trans-trans isomer of 4,4'-HMDA must lie within a certain range. Besides the other geometric isomers which are obtained by the hydrogenation of 4,4'-diamino-diphenylmethane (4,4'-MDA), namely the cis-cis and the cis-trans isomers, the content of the trans-trans isomer of 4,4'-HMDA in the hydrogenated product must be about 15 to 40%, preferably about 15 to 30% and most preferably about 18.5 to 23% by weight, based on the diamine content of the hydrogenated product, in order to subsequently obtain a diisocyanate which remains liquid.

There are a series of known methods by which MDA is hydrogenated with different catalysts without considering the amount of trans-trans isomer which is obtained. As an example, U.S. Pat. Nos. 3,155,724, 3,644,522, and 3,766,272 should be mentioned. In these hydrogenation processes the trans-trans content can reach the thermodynamically theoretical value of 50 to 55% by weight. Thus, the trans-trans content of 4,4'-HMDA in the hydrogenated product has to be reduced from an average of 50 to 55% by weight down to the above-mentioned ranges through an additional separation process. Further, if there are no uses for the trans-trans isomer enriched mixture, the process suffers from low yields and high costs and is therefore an uneconomical way to produce 4,4'-HMDA with a low content of the trans-trans isomer.

Among the different catalysts, e.g., Co or Mn catalysts on inert supports (e.g. U.S. Pat. No. 3,743,677), rhodium/aluminum oxide catalysts on inert supports (e.g. German Patent 2,423,639), iridium/aluminum oxide catalysts on inert supports (e.g. U.S. Pat. No. 3,914,307), ruthenium catalysts on inert supports (e.g. U.S. Pat. Nos. 2,606,925, 2,606,928, 3,347,917, 3,636,108, 3,676,495 and European Patents 66,210, 111,238) or ruthenium dioxide (e.g. U.S. Pat. Nos. 2,494,563, 2,606,924, 3,742,049 and European Patent 66,211), it is known that rhodium and ruthenium catalysts are specifically suited for the hydrogenation of MDA, especially if a high selectivity for 4,4'-HMDA with a simultaneously low content of the trans-trans isomer is desired.

The previous processes which used ruthenium catalysts (see e.g. U.S. Pat. Nos. 2,494,563, 2,606,924, 2,606,925, 2,606,928, 3,347,917, 3,676,495, 3,959,374, 3,743,677, 3,914,917, 3,825,586, 3,636,108, and 4,161,492) resulted in amine mixtures with sufficiently low trans-trans isomer contents. However, the rates of reaction are too slow to yield technically interesting yields of 4,4'-HMDA. More recent processes using ruthenium catalysts (e.g., European Patents 66,210 and 66,211) result in low trans-trans isomer contents with technically interesting rates of reaction, but they have the disadvantage that because of by-product formation the yields of 4,4'-HMDA are low (less than 95%) and also the catalysts have a short lifetime. The same is true for the known processes using rhodium catalysts (e.g., European Patent 66,212); a fact which makes such processes technically uninteresting, notwithstanding the comparatively higher price of rhodium.

In European Patent 111,238 a catalyst containing 5% ruthenium on an inert support which is treated with a nitrate or sulfate of an alkali or alkaline earth metal is described. The use of this catalyst in a slurry process provides a 93% yield of 4,4'-HMDA having a trans/trans content of 23% as reported in Example 1 of that patent. In U.S. Pat. No. 3,636,108 and 3,697,449, other alkali and alkaline earth metals are used with ruthenium supported powdered catalysts to produce catalyst systems which can be used in slurry processes to give high yields of 4,4'-HMDA. Without the use of such promoters, the powdered ruthenium catalysts produce significant amounts of polymeric material. (See the comparison examples in this application and Example 13 in EP 111,238). However, it has been discovered that the fixed bed process described herein produces insignificant amounts of polymerics without the use of promotors using process conditions which are similar to those of the above-cited patent examples. (Also, see Table 1 of this application). Another disadvantage of the slurry process is that the catalyst must be separated from the product and recycled.

It is an object of the present invention to provide a process which does not have the above disadvantages and which is capable of hydrogenating MDA with high selectivity and high catalyst activity, i.e. a process which results in high throughputs of MDA to HMDA containing about 15 to 40 weight percent, preferably about 15 to 30 weight percent, more preferably 18.5 to 23.5 weight percent and most preferably about 23 weight percent of the trans-trans isomer of 4,4'-HMDA, based on the diamine content of the hydrogenated product. It is a further object of the present invention to provide an economical process which is capable of continuous operation, preferably without solvents, and results in a high, if not complete, conversion of MDA. Also, the catalyst should have a long lifetime. These objectives can be achieved according to the present invention as set forth hereinafter.

SUMMARY OF THE INVENTION

The present invention is directed to a process for the catalytic hydrogenation of a starting material containing 4,4'-diamino-diphenylmethane (4,4'-MDA) or its mixtures with 2,4'-diamino-diphenylmethane, 2,2'-diamino-diphenylmethane and/or higher ring compounds of the diphenylmethane series to a hydrogenation product having a trans-trans isomer content of 4,4'-diamino-dicyclohexylmethane (4,4'-HMDA) of about 15 to 40 weight percent, based on the diamine content of the hydrogenated product, by continuously hydrogenating in at least one fixed bed reactor at a temperature of about 100° to 190° C. and a pressure of about 50 to 350 bar in the presence of a ruthenium catalyst on a catalyst support having a BET surface area of about 70 to 280 m²/g and an average pore diameter $d_p$ of about 10 to 320 Å, the catalyst being prepared by impregnating the catalyst support to a penetration depth of at least about 50 µm with a soluble ruthenium compound in an amount sufficient to provide a catalyst containing about 0.1 to 5 weight percent ruthenium and subsequently reducing the soluble ruthenium compound to ruthenium.

DETAILED DESCRIPTION OF THE INVENTION

In accordance with the present invention the above starting material (MDA) is hydrogenated with a ruthenium catalyst on an inert support at a temperature of about 90° to 190° C., preferably about 100° to 170° C. and a pressure of about 50 to 350 bar, preferably 130 to 350 bar. The continuous hydrogenation is conducted in a fixed bed reactor and can be run in a countercurrent or a concurrent mode. The concurrent process is preferred. The process may be conducted with product recycling and/or gas recycling. Preferred is the embodiment where the gas is recycled and the product is not recycled. The hydrogenation can also be run in several fixed bed reactors which are assembled in series and which are preferably run concurrently. The hydrogenation is carried out preferably in the trickle phase.

Suitable starting materials include pure 4,4'-diaminodiphenylmethane (4,4'-MDA) or its mixtures with 2,4'- and/or 2,2'-diamino-diphenylmethane and/or with the higher polyamine homologs of the diphenylmethane series (higher ring compounds or polymerics). Preferred raw materials contain about 70 to 100 weight percent, preferably about 80 to 100 weight percent of 4,4'-, 2,4'- and/or 2,2'-diamino-diphenylmethane and 0 to about 30 weight percent, preferably 0 to about 20 weight percent of compounds containing more than two aromatic rings. The starting material should contain a minimum of 40 weight percent 4,4'-MDA. Preferred starting materials contain a minimum of 70 weight percent, more preferably 75 weight percent 4,4'-MDA. When larger amounts of 2,4'-MDA are present, liquid hydrogenated products may be obtained with higher trans-trans isomer contents of 4,4'-HMDA, i.e., up to about 40 weight percent, preferably up to about 30 weight percent. If the hydrogenation process is conducted in the presence of higher ring compounds (polymerics), then these products are generally separated subsequent to the hydrogenation process, e.g., by distillation. After separation of the hydrogenated higher ring compounds the diamine products may be phosgenated to the corresponding diisocyanate.

The hydrogenation may be conducted with or without solvent, preferably without solvent. Suitable solvents include alcohols such as methanol, ethanol, n-propanol, isopropanol, n-butanol, isobutanol and tertiary butanol; acyclic and cyclic ethers such as isopropylether, n-butylether, tetrahydrofuran and 1,4-dioxane; and hydrocarbons such as cyclohexane. A preferred solvent is tert. butanol with or without minor amounts of isobutanol. The ratio of starting material to solvent may lie in the range of about 1:0 to 1:4, preferably about 4:1 to 1:4 and most preferably about 1:1 to 1:3.

The ruthenium content of the catalyst including the catalyst support is about 0.1 to 5 weight percent, preferably about 0.5 to 3.0 weight percent with a penetration depth of the soluble ruthenium compound into the outer surface of the catalyst support of at least about 50 µm, preferably about 50 to 600 µm, more preferably 50 to 500 µm and most preferably about 100 to 300 µm. Suitable ruthenium compounds include hydrated ruthenium trichloride, hexamine ruthenium, aquopentamine and diaquotetramine ruthenium salts of chlorine. Hydrated ruthenium trichloride is the preferred ruthenium compound. The catalyst support may be treated with the ruthenium salt in an amount sufficient to achieve the disclosed ranges of ruthenium and the required penetration depth. The catalyst support is then dried and the salt is reduced to the noble metal at temperatures of about 100° to 400° C., preferably about 150° to 350° C. with either hydrogen or a mixture of hydrogen and an inert gas such as nitrogen or a noble gas, e.g., argon.

All compounds which are inert in the reaction may be used as catalyst supports such as charcoal, oxides of aluminum and silicones as well as their mixtures, for example Fuller's earth, clay, kaolin, bentonite, kieselgur, silica gel, diatomaceous earth, bauxite, and especially high purity aluminum oxide. The BET surface of the catalysts is generally about 70 to 280 m²/g, preferably about 90 to 280 m²/g, and the average pore diameter $d_p$ is about 10 to 320 Å. The preferred catalyst support is a pure aluminum oxide with a BET surface of about 200 to 250 m²/g ($O_{BET}$=200 to 250 m²/g) and an average pore diameter of about 100 Å to 150 Å ($d_p$=100 to 150 Å), especially in the form of an extrudate (strands) with a mean diameter $d_K$ of 1.6 mm and a mean length $l_K$ of 4 mm.

The loading of starting material (MDA) based on the catalyst mass is established at a liquid hourly mass velocity, LHMV (MDA), of about 0.08 to 0.4 g of MDA per gram of catalyst per hour. The specific catalyst performance which can be reached with regard to the trans-trans isomer, based on the amount of ruthenium, is in the specific catalyst performance (SKL) range of about 1 to 10 g of trans-trans 4,4'-HMDA per gram of ruthenium per hour (see Table 1).

The process according to the invention is suited to produce 4,4'-diamino-dicyclohexylmethane with the desired low contents of the trans-trans isomer and with high selectivity and high catalyst performance. The process according to the invention has the advantage that HMDA with the desired trans-trans isomer content of 4,4'-HMDA is obtained for a long period of time with high selectivity and high catalyst activity. Also, the process has the advantages present from using a fixed bed process in which the hydrogenation is preferably carried out in the trickle phase as previously discussed.

The chlorine content of the MDA should be kept preferably in the range of up to about 5 ppm to minimize the formation of higher ring compounds. Nevertheless, even at higher chloride contents, there is no deterioration of the catalyst; however, the chloride must be washed off from time to time with water to prevent an excessive enrichment of chloride on the catalyst surface. This water washing can be done with the catalyst of the invention without any activity or selectivity loss.

The following examples exemplify the invention. The invention is further illustrated but is not intended to be limited by the following examples in which all parts and percentages are by weight unless otherwise specified.

EXAMPLES

Example 1

400 ml = 220 g of a ruthenium on aluminum oxide catalyst with a ruthenium content of 1 weight percent and a penetration depth of the impregnated outer layer of 90 μm, a BET surface of 205 m²/g and an average pore diameter $d_K$ of 128 Å were placed into a continuously operable fixed bed reactor with gas recycling. The catalyst had the shape of an extrudate with a mean diameter $d_K$ of 1.6 mm and a mean length $l_K$ of 4 mm. The reactor was loaded at T=110° C. and P=300 bar with a mixture of 4,4'-MDA and butanol (90% tert. butanol and 10% isobutanol) in a weight range of 1:3 and with hydrogen. The loading of MDA, based on the catalyst mass, was established at an LHMV (MDA)=0.12 g of MDA/g of catalyst per hour. The hydrogenation was carried out in the trickle phase.

After 840 hours a product was obtained with 97.2 weight percent of 4,4'-HMDA having a trans-trans content of 20.5 weight percent. The activity and the selectivity of the catalyst at a 100% conversion of MDA [U(MDA)=100 mol %] were unchanged during the whole period. The hydrogenated product also contained 0.39 weight percent of 4,4'-diamino-cyclohexyl-phenylmethane (1/2 HMDA) and 0.94 weight percent of three and four ring compounds. The specific catalyst performance (SKL) with respect to the trans-trans isomer formation of 4,4'-HMDA, based on ruthenium, was 2.1 g trans-trans 4,4'-HMDA per g/Ru per hour (see Table 1).

Example 2

Example 1 was repeated using 250 g of catalyst. After 528 hours, the values which were obtained are summarized in Table 1.

After 528 hours operation time a mixture of 30 weight percent 4,4'-MDA and 70 weight percent HMDA (without solvent) was fed into the reactor at a temperature of 125° C. and a loading of LHMV (MDA)=0.1, and the hydrogenation was continued. After a hydrogenation time of 936 hours, the values which were obtained (see Table 1) demonstrate that the process can be run without solvent, with high activity and simultaneously high selectivity, to hydrogenate MDA to HMDA with a trans-trans isomer content of 4,4'-HMDA, based on the mixture, of about 23 weight percent.

Example 3

21 kg of the catalyst used in Example 1 were filled into a continuously operable fixed bed reactor with gas recycling. The reactor was loaded at a temperature T=130° C. and P=300 bar with a mixture of 4,4'-MDA and tertiary butanol in a weight range of 1:1 and the whole system was pressurized with hydrogen. A loading of LHMV (MDA)=0.15 kg of MDA per kg of catalyst per hour was used. After 216 hours a hydrogenated product which had the properties summarized in Table 1 was obtained.

Example 4

A continuously operating apparatus consisting of two fixed bed reactors in series was filled with the catalyst described in Example 1, 200 liters of catalyst for reactor No. 1 and 120 liters of catalyst for reactor No. 2. 34 liters of 4,4'-MDA per hour were run through this system. The heat exchange in the first reactor was accomplished with product recycling; the recycled amount was in the range of the 1 to the 40-fold amount of material fed into Reactor 2. The temperature in the first reactor was between 130° and 160° C. and the conversion was in the range of 90%. The remaining non-hydrogenated 4,4'-MDA was hydrogenated in Reactor 2 with direct throughput (about 10 Nm³ per hour of gas at 120° to 140° C.). The pressure in both reactors was about 300 bar.

After 2,500 hours, the values which were obtained are summarized in Table 1.

Example 5

In the same reactor as described in Example 1, a catalyst having a ruthenium content of 2.5% was used. The penetration depth of the ruthenium was 145 m, the BET surface of the catalyst support was 230 m²/g, and the average pore diameter was 115 Å. The starting material was a solvent-free MDA starting material having a two-ring content of 91.5%, a polymerics content of 8.5% and a 4,4'-MDA content of about 80%. After an operation time of 264 hours, T=125° C., and a pressure of P=300 bar, the average analytical values which were obtained are summarized in Table 1.

Example 6

A continuously operating fixed bed reactor with gas recycling was filled with 20 liters=11 kg of the catalyst described in Example 1. At 130° C., the reactor was put under 300 bar hydrogen pressure and loaded with 2 kg/h of 4,4'-MDA per hour (LHMV: 0.18 kg MDA/kg catalyst per hour). Activity and selectivity of the catalyst remained practically constant over a period of 528 hours. The average analytical values are summarized in Table 1.

The content of half-reduced MDA after distillation was recycled into the reactor.

Example 7

A continuously operating hydrogenation unit (as in Example 4) with two fixed bed reactors in series which were run concurrently was filled with the catalyst described in Example 1, 400 kg of catalyst into Reactor 1 and another 185 kg of catalyst into Reactor 2. The temperature in Reactor 1 was $T_I$=130° to 142° C. and in Reactor 2 was $T_{II}$=117° to 137° C.; a pressure of 300 bar of hydrogen was maintained. A solvent-free 4,4'-MDA was hydrogenated at a loading of 0.26 kg of MDA per kg of catalyst per hour. The heat exchange in Reactor 1 was accomplished by recycling product at a rate of 65 kg of recycled material per kg of input. The amount of hydrogen run through both reactors was between 100 and 200 Nm³ per hour.

The reaction product contained, on an average basis, 82 to 83 weight percent of 4,4'-HMDA, 11 to 12 weight percent 1/2 HMDA, 2 to 3 weight percent 4,4'-MDA and 2 to 3 weight percent of three and four ring compounds. The average trans-trans content of 4,4'-HMDA, based on the mixture, was 23.5 weight percent. A total of 243 tons of 4,4'-MDA were hydrogenated with this catalyst.

Example 8

A continuously operable 1.5 m³ fixed bed reactor with gas recycling was filled with 878 kg of the catalyst described in Example 1. 585 kg of this catalyst had already been used to hydrogenate 243 tons of 4,4'-MPA (see Example 7). At 300 bar hydrogen pressure and a reaction temperature of T=118° to 165° C. the catalyst was loaded at a rate of 0.14 kg/kg catalyst per hour with a solvent-free, MDA starting material having a two-ring content of 90%, a polymeric content of 10% and a 4,4'-MDA content of about 78%. The amount of recycled gas was 4,500 Nm³ of hydrogen/hour. The hydrogenated products (see Table 1) contained 85 to 86 weight percent of 4,4'-HMDA. The conversion was practically complete, i.e. the hydrogenated product contained 0.5 weight percent half-reduced MDA and no MDA. The amount of three- and four-ring compounds in the reaction product was between 3.5 and 4 weight percent in addition to the 10% of higher boiling higher ring compounds which were already present in the starting material. The average trans-trans content of 4,4'-HMDA, based on the mixture, was 23.3 weight percent.

After 600 hours the run was stopped. Activity and selectivity of the catalyst remained constant during the whole period. Including the 2,769 hours of operation time of the 585 kg of used catalyst present in the catalyst mixture, the total average operation time of the catalyst was 2,442 hours.

Example 9

380 g=400 ml of a commercial 1% ruthenium-/aluminum oxide catalyst were filled into a fixed bed reactor according to Example 1. The penetration depth of the outer-zone-impregnated catalyst was 0.6 mm, the BET surface of the catalyst support was 80 m²/g and the average pore diameter was 240 Å. At T=110° C. and P=300 bar, the reactor was loaded with a mixture of 4,4'-MDA and butanol (90 weight percent tertiary butanol and 10 weight percent isobutanol) in a weight ratio of 1:3 and with hydrogen. The throughput of the reactor was established at 0.04 kg of MDA per kg of catalyst per hour. This throughput provided a practically complete hydrogenation of 4,4'-MDA. After 192 hours of operation time, the activity of the catalyst was unchanged. The analytical data of the hydrogenated product is summarized in Table 1. After 240 hours of operation time a 4,4'-MDA/solvent ratio of 1:1 was established and the hydrogenation continued for further 120 hours with a throughput of 4,4'-MDA of LHMV (MDA)=0.1 kg MDA per kg of catalyst per hour under otherwise the same conditions. The analysis of the hydrogenated product which was obtained after 360 hours of operation time is summarized again in Table 1.

Examples 10 and 11 Comparison

The slurry phase experiments were carried out in a one-liter stainless steel autoclave fitted with internal cooling coils, thermometer, magnetic stirrer, and an external electrical heating mantel. A 5% Ru/Al₂O₃ catalyst in dry powder form was used in the experiments.

The reactions were carried out in the following manner. After sealing the autoclave with the 4,4'-MDA and catalyst inside, the autoclave was pressurized to the desired pressure, the stirrer was started, and heating was begun. The temperature was allowed to climb to the desired reaction temperature, at which point it was manually controlled (±3° C.) by intermittently running water through the cooling coils. The pressure was maintained (± about 20 bar) by manually introducing hydrogen into the reactor throughout the reaction. The reaction was considered complete when no further pressure drop was noted. The reaction time was recorded as the time from initial hydrogen uptake to the point where no further pressure drop occurred. The results of the gas chromatographic analysis are listed below.

| Catalyst wt. % | MDA g | Temp./Press. °C./bar | Rxn Time min. | % t/t Area % | HMDA Area % | 4-Ring Area % |
|---|---|---|---|---|---|---|
| 2.5 | 400 | 160/275 | 80 | 25.5 | 87.0 | 13.0 |
| 3.8 | 400 | 160/275 | 46 | 26.5 | 91.1 | 8.9 |

TABLE I

| Ex. No. | operation time hr | Temp. °C. | MDA/ solvent | HMDA/ MDA | LHMV (MDA) g/MDA g Cat. × h | HMDA wt. % | ½ HMDA wt. % | MDA wt. % | 3 or 4 ring isomers | Higher ring compounds wt. % | Trans-Trans HMDA wt. % | SKL g tr.-tr.-HMDA/g Ru × h wt. % |
|---|---|---|---|---|---|---|---|---|---|---|---|---|
| 1 | 840 | 110 | 1:3 | — | 0.12 | 97.2 | 0.39 | — | 0.94 | — | 20.5 | 2.1 |
| 2 | 528 | 110 | 1:3 | — | 0.12 | 95.7 | — | — | 2.62 | 0.02 | 21.1 | 2.2 |
|   | 936 | 125 | — | 7:13 | 0.1 | 96.0 | 0.18 | — | 2.98 | 0.67 | 22.1 | 1.9 |
| 3 | 216 | 130 | 1:1 | — | 0.15 | 96.5 | — | — | 1.54 | 0.01 | 22.4 | 2.9 |
| 4 | 2500 | 130–160 120–140 | — | 1–40 | 0.18 | 90.5 | 4.6 | 0.2 | 4.0 | 0.4 | 22.6 | 3.3 |
| 5 | 264 | 125 | — | — | 0.3 | 87.8 | 3.7 | — | 8.5 | 0.3 | 21.5 | 5.0 |
| 6 | 528 | 130 | — | — | 0.18 | 93.7 | 4.1 | — | 2.1 | 0.1 | 22.7 | 3.4 |
| 7 | 2769 | 130–142 | — | — | 0.26 | 82–83 | 11 12 | — | 2–3 | 0.3 | 23.5 | 5.1 |
| 8 | 2442 | 118–165 | — | — | 0.14 | 85–86 | 0.5 | — | 3.5–4.5 | 0.7 | 23.3 | 3.3 |
| 9 | 192 | 110 | 1:3 | — | 0.04 | 95.9 | 0.1 | — | 1.82 | — | 25.9 | — |
|   | 360 | 110 | 1:1 | — | 0.1 | 93.7 | 2.12 | 0.11 | 2.47 | 0.23 | 20.5 | 1.7 |

The preceding results demonstrate that the process of the present invention when compared with prior art processes produces a 4,4'-HMDA with a low trans-trans isomer content by the catalytic hydrogenation of 4,4'-HMDA using a catalyst having a combination of higher activity and higher selectivity.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the catalytic hydrogenation of a starting material comprising 4,4'-diamino-diphenylmethane or its mixture with 2,4'-diamino-diphenylmethane, 2,2'-diamino-diphenylmethane and/or higher ring compounds of the diphenylmethane series to a hydrogenation product having a trans-trans isomer content of 4,4'-diamino-dicyclohexylmethane of about 15 to 40 weight percent and containing a higher yield of 4,4'-diamino-dicyclohexylmethane isomers and a smaller content of polymerics than when said starting material is hydrogenated in a corresponding slurry phase process which comprises continuously hydrogenating said starting material in at least one fixed bed reactor at a temperature of about 100° to 190° C. and a pressure of about 50 to 350 bar in the presence of a ruthenium catalyst on a catalyst support having a BET surface area of about 70 to 280 m$^2$/g and an average pore diameter $d_p$ of about 10 to 320 Å, said catalyst being prepared by impregnating said catalyst support to a penetration depth of at least about 50 μm with a soluble ruthenium compound in an amount sufficient to provide a catalyst containing about 0.1 to 5 weight percent ruthenium and subsequently reducing said soluble ruthenium compound to ruthenium.

2. The process of claim 1 wherein said soluble ruthenium compound comprises hydrated ruthenium trichloride.

3. The process of claim 1 wherein said catalyst has a ruthenium content of about 0.5 to 3 weight percent.

4. The process of claim 1 wherein said catalyst support is treated to a penetration depth of about 100 to 300 μm.

5. The process of claim 1 wherein said catalyst support is a high purity aluminum oxide with a BET surface area of about 200 to 250 m$^2$/g and an average pore diameter $d_p$ of about 100 to 150 Å.

6. The process of claim 1 wherein said hydrogenation is conducted concurrently with gas recycling, but without product recycling.

7. The process of claim 1 wherein said hydrogenation is conducted in the trickle phase.

8. The process of claim 1 wherein said hydrogenation is conducted in the present of a solvent comprising tert. butanol 9. The process of claim 8 wherein said solvent additionally comprises isobutanol.

10. A process for the catalytic hydrogenation of a starting material comprising 4,4'-diamino-diphenylmethane or its mixture with 2,4'-diamino-diphenylmethane, 2,2'-diamino-diphenylmethane and/or higher ring compounds of the diphenylmethane series, said starting material having a content of 4,4'-diamino-diphenylmethane of at least about 75 weight percent, to a hydrogenation product having a trans-trans isomer content of 4,4'-diamino-dicyclohexylmethane of about 15 to 30 weight percent and containing a higher yield of 4,4'-diamino-dicyclohexylmethane isomers and a smaller content of polymerics than when said starting material is hydrogenated in a corresponding slurry phase process which comprises continuously hydrogenating said starting material in at least one fixed bed reactor at a temperature of about 100° to 190° C. and a pressure of about 50 to 350 bar in the presence of a ruthenium catalyst on a catalyst support having a BET surface area of about 200 to 250 m$^2$/g and an average pore diameter $d_p$ of about 100 to 150 Å, said catalyst being prepared by impregnating said catalyst support to a penetration depth of about 100 to 300 μm with hydrated ruthenium trichloride in an amount sufficient to provide a catalyst containing about 0.5 to 3 weight percent ruthenium and subsequently reducing said hydrated ruthenium chloride to ruthenium.

11. The process of claim 9 wherein said hydrogenation is conducted concurrently with gas recycling, but without product recycling.

12. The process of claim 9 wherein said hydrogenation is conducted in the presence of a solvent comprising tert. butanol.

13. The process of claim 11 wherein said solvent additionally comprises isobutanol.

* * * * *